(12) United States Patent
Buelow et al.

(10) Patent No.: US 9,014,448 B2
(45) Date of Patent: Apr. 21, 2015

(54) ASSOCIATING ACQUIRED IMAGES WITH OBJECTS

(75) Inventors: Thomas Buelow, Grosshansdorf (DE); Kirsten Meetz, Hamburg (DE); Martin Bergtholdt, Hamburg (DE); Johannes Buurman, Eindhoven (NL); Axel Saalbach, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 82 days.

(21) Appl. No.: 13/516,576

(22) PCT Filed: Nov. 24, 2010

(86) PCT No.: PCT/IB2010/055386
§ 371 (c)(1),
(2), (4) Date: Jun. 15, 2012

(87) PCT Pub. No.: WO2011/073832
PCT Pub. Date: Jun. 23, 2011

(65) Prior Publication Data
US 2012/0243765 A1 Sep. 27, 2012

(30) Foreign Application Priority Data
Dec. 18, 2009 (EP) .................................... 09179838

(51) Int. Cl.
*G06K 9/00* (2006.01)
*G06F 19/00* (2011.01)

(52) U.S. Cl.
CPC .................................. *G06F 19/321* (2013.01)

(58) Field of Classification Search
None
See application file for complete search history.

(56) References Cited

U.S. PATENT DOCUMENTS

| 5,604,956 A | 2/1997 | Grass |
| 5,954,650 A | 9/1999 | Saito et al. |
| 2004/0254503 A1 | 12/2004 | Sarvazyan et al. |
| 2007/0036402 A1 | 2/2007 | Cahill et al. |

(Continued)

FOREIGN PATENT DOCUMENTS

| JP | 2007330419 A | 12/2007 |
| JP | 2008132109 A | 6/2008 |

(Continued)

OTHER PUBLICATIONS

Sanjay-Gopal, "A Regional Registration Technique for Automated Interval Change Analysis of Breast Lesions on Mammograms" Medical Physics, vol. 26, No. 12, Dec. 1999, pp. 2669-2679.
Levin et al, "Retrospective Geometric Correlation of MR, CT, and PET Images", Radiology, vol. 169, 1988, pp. 817-823.

*Primary Examiner* — Nirav G Patel

(57) ABSTRACT

A system for associating acquired images with objects is disclosed. It comprises an image selector (1) for selecting a stored image from a database (5) comprising a plurality of stored images, the database (5) comprising an association (21) between the stored image (6) and an object of interest; an image scanner (2) for acquiring a new image (9) comprising a representation (10) of at least part of the object of interest, during an imaging session; a user interface (3) for enabling a user, during the imaging session, to indicate that the new image (9) is to be associated with the object of interest; and an associating subsystem (4) for creating an association (23) between the new image (9) and the object of interest in the database. The user interface (3) is arranged for enabling a user to select the object of interest from a plurality of objects of interest associated with the stored image (6).

18 Claims, 3 Drawing Sheets

(56) References Cited

U.S. PATENT DOCUMENTS

| | | | |
|---|---|---|---|
| 2007/0081712 A1 | 4/2007 | Huang et al. | |
| 2008/0193004 A1* | 8/2008 | Mine | 382/131 |
| 2009/0087049 A1* | 4/2009 | Takahashi | 382/128 |
| 2009/0226065 A1 | 9/2009 | Chen | |
| 2009/0292559 A1* | 11/2009 | Ranjan et al. | 705/3 |
| 2009/0312640 A1* | 12/2009 | Wang et al. | 600/443 |

FOREIGN PATENT DOCUMENTS

| | | |
|---|---|---|
| WO | 2006119340 A2 | 11/2006 |
| WO | 2008062415 A2 | 5/2008 |

* cited by examiner

ASSOCIATING ACQUIRED IMAGES WITH OBJECTS

FIELD OF THE INVENTION

The invention relates to associating acquired images with objects. The invention further relates to associating acquired images with lesions.

BACKGROUND OF THE INVENTION

Breast cancer diagnosis nowadays may be based on multiple imaging modalities (x-ray mammography, ultrasound (US), and/or magnetic resonance (MR), for example). Frequently, a patient has more than one lesion, and multiple lesions may be visible in a single prior mammogram or MR exam. When an additional ultrasound image of the same patient is acquired, only coarse location information of the ultrasound image is stored, for example based on the location of the ultrasound probe. This location information is entered manually by a healthcare professional.

US 2007/0036402 A1 discloses a system for the detection of abnormalities in a medical image of a subject. With this system, x-ray mammographic and ultrasound images of the breast are captured to form an examination bundle. Candidate masses are identified in the x-ray mammographic image, using techniques known to those skilled in the art. A correspondence is established between the x-ray mammographic image and the ultrasound image by identifying the region or regions in the ultrasound image corresponding to any identified candidate masses in the x-ray mammographic image.

SUMMARY OF THE INVENTION

It would be advantageous to have an improved way of associating acquired images with objects. To better address this concern, a first aspect of the invention provides a system comprising
  an image selector for selecting a stored image from a database comprising a plurality of stored images, the database comprising an association between the stored image and an object of interest;
  an image scanner for acquiring a new image comprising a representation of at least part of the object of interest, during an imaging session;
  a user interface for enabling a user, during the imaging session, to indicate that the new image is to be associated with the object of interest; and
  an associating subsystem for creating an association between the new image and the object of interest in the database.

The best time to associate an image with the object of interest represented by the image may be the time of acquiring the image, because the person acquiring the image may at that time have the knowledge about what object is represented by the image. If it is attempted to make the association later, retrospectively, this may be much more difficult, because the position of the new image with respect to the stored image may not be available in retrospective analysis. This may be the case for example when the image scanner is a hand-held device, such as an ultrasound probe or a hand-held camera.

The user interface may be arranged for enabling a user to select the object of interest from a plurality of objects of interest associated with the stored image. This way, it is possible to handle the case where a plurality of objects of interest are associated with a stored image.

The database may comprise an association between the object of interest and a position of the object of interest in the stored image. This allows providing advanced functionality, for example by visualizing an indication of the object of interest in the stored image.

The user interface may be arranged for enabling a user to select the object of interest by indicating the position of the object of interest in the stored image. This is an intuitive way of selecting the object of interest.

The associating subsystem may be arranged for storing in the database an association between the object of interest and a position of the object of interest in the new image. This allows providing more detailed information about the location of the object of interest in the new image.

The user interface may be arranged for enabling a user to indicate the position of the object of interest in the new image. This is an efficient way for the system to gain knowledge of the position of the object of interest. With this knowledge, the system may create the association between the object of interest and its position in the new image.

The image selector may be arranged for selecting the stored image or the object of interest before the new image is acquired. This makes the process more efficient, because the user can actively look for the relevant object of interest during the image acquisition.

The system may comprise a graphical subsystem for displaying the stored image during a time interval comprising a time of acquiring the new image and a time of indicating that the new image is to be associated with the object of interest. This makes it easier for the user to localize the object of interest in the patient while acquiring the new image.

The user interface may be provided at least in part on the image scanner. This allows the user to easily indicate that the image is associated with the object of interest, because the user is already working with the image scanner. For example, the user may indicate via the image scanner that the current image is to be associated with the object of interest.

The stored image and the new image may be breast images, and the object of interest may comprise a breast lesion. This is a useful application domain of the system.

The image scanner for acquiring the new image may comprise an ultrasound scanner. This way, images made with a hand-held scanner may be properly associated with the relevant object(s) of interest.

The system may comprise a medical workstation, and the image selector (1), the user interface (3), and/or the associating subsystem (4) may be implemented at least partly in software arranged for running on the medical workstation. This is an efficient realization possibility of the system.

Another aspect of the invention provides a medical image acquisition apparatus comprising the system set forth. Another aspect of the invention provides a medical workstation comprising the system set forth.

Another aspect of the invention provides a method of associating acquired images with objects, comprising
  selecting a stored image from a database comprising a plurality of stored images, the database comprising an association between the stored image and an object of interest;
  acquiring a new image comprising a representation of at least part of the object of interest, during an imaging session;
  enabling a user, during the imaging session, to indicate that the new image is to be associated with the object of interest; and
  creating an association between the new image and the object of interest in the database.

Another aspect of the invention provides a computer program product comprising instructions for causing a processor system to perform the method set forth.

It will be appreciated by those skilled in the art that two or more of the above-mentioned embodiments, implementations, and/or aspects of the invention may be combined in any way deemed useful.

Modifications and variations of the image acquisition apparatus, the workstation, the system, and/or the computer program product, which correspond to the described modifications and variations of the system, can be carried out by a person skilled in the art on the basis of the present description.

A person skilled in the art will appreciate that the method may be applied to multi-dimensional image data, e.g. two-dimensional (2-D), three-dimensional (3-D) or four-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

Figure 1:
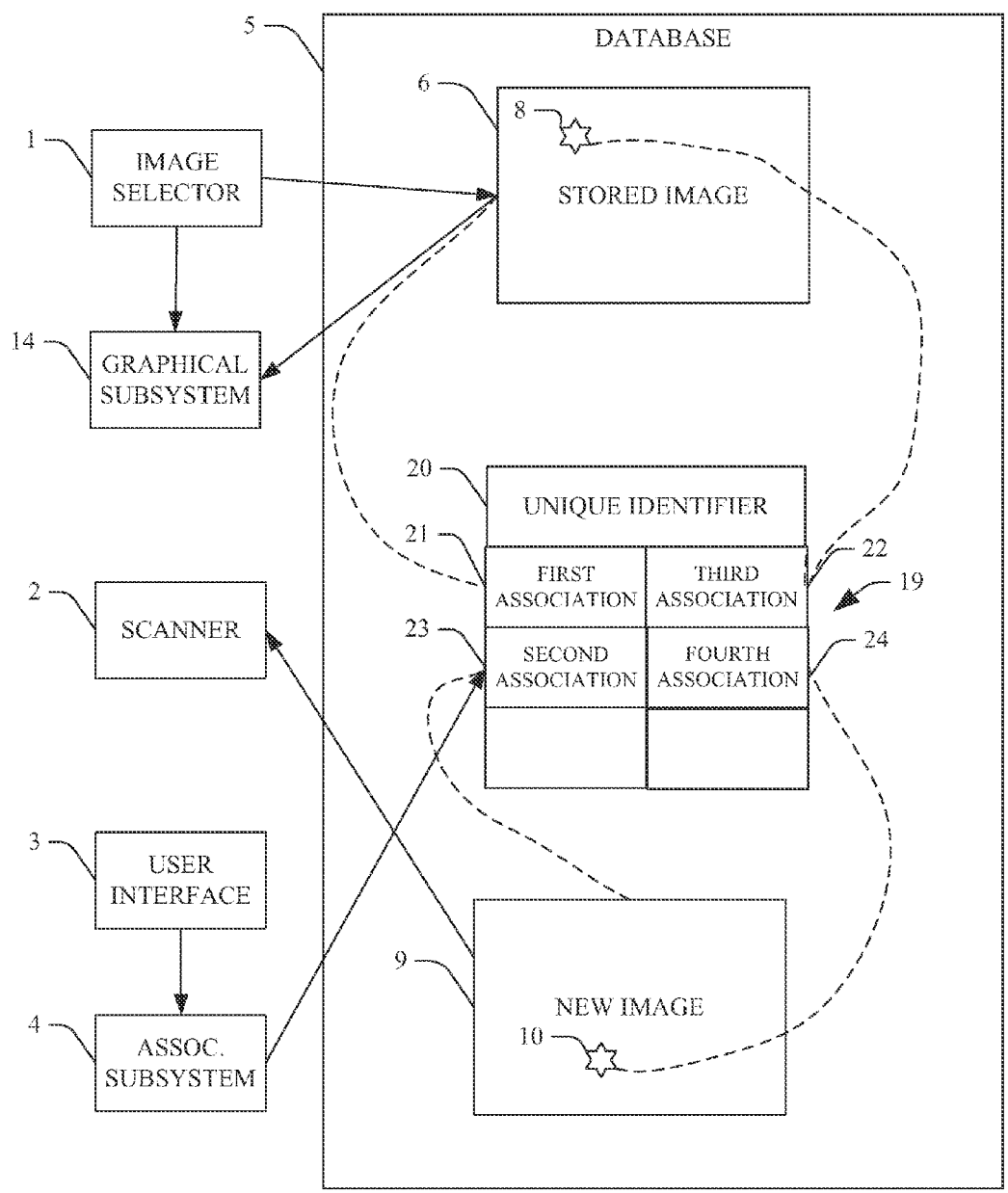
FIG. 1 is a diagram of a system for associating acquired images with objects.

FIG. 1 illustrates, in a diagrammatic way, aspects of a system for associating acquired images with objects. Such association may be helpful when interpreting the acquired images. In particular, objects appearing in a plurality of acquired images may be linked to each other by means of such associations. The system may comprise a database 5 which may comprise images and associations. Alternatively, it is also possible that the system comprises a communications subsystem for communicating with an external database. The system may further comprise an image selector 1 for selecting a stored image from the database 5. The database 5 may have stored therein an association 21 between the stored image 6 and an object of interest.

The system may comprise an image scanner 2 for acquiring a new image 9. Such a newly acquired image may comprise a representation of at least part of the object of interest, as shown at position 10 in the new image 9. In this case, the user may indicate that the image comprises this representation of at least part of the object of interest. To this end, a user interface 3 may be provided for enabling a user to indicate that the new image 9 is to be associated with the object of interest. The user interface 3 may be arranged for allowing the user to make this indication during the imaging session during which the new image 9 is acquired, for example, while the patient is still there and more images may be acquired by the user.

The system may comprise an associating subsystem 4 for creating an association 23 between the new image 9 and the object of interest in the database.

It is noted that associations may be represented in the database 5 in several different ways. One possible representation of an association, illustrated in FIG. 1, comprises a table 19. The table 19 may have an object identifier 20, which may be a random identifier, or alternatively, a descriptive text identifier. However, such an identifier is optional and may take a different form. Further information about the object of interest may also be stored, as desired. The table may further comprise associations with images and/or positions in images. Such associations may be represented by means of identifiers of images, and/or coordinates, respectively. In table 19, the left column comprises associations 21, 23 with images, for example in form of image identifiers, and the right column comprises associations 22, 24 with positions in the respective images 21, 23. These associations with positions may comprise image coordinates, for example. Other kinds of representations of associations are also possible, for example using memory pointers to images or to specific parts of images. The dashed lines in FIG. 1 indicate the images and positions which are the subject of the associations 21, 22, 23, 24. For example, association 21 provides an association of the object of interest with image 6, and association 22 (together with association 21) provides an association of the object of interest with position 8 in image 6. Consequently, the associating subsystem 4 may be arranged for creating the association 23 associating the new image 9 with the object of interest, for example by including an identifier of image 9 in the table 19.

The user interface 3 may be arranged for enabling a user to select the object of interest from a plurality of objects of interest associated with the stored image 6. For example, a plurality of tables similar to table 19 may be available, each table relating to a different object of interest. It is possible that more than one of these tables defines an association with the same stored image 6. In such a case, the user interface 3 may allow selecting a particular one of these objects of interest which are associated with the stored image 6. This allows the associating subsystem to create the association between the new image 9 and the particular selected object of interest. It is also possible to enable the user to select a plurality of objects with which the new image 9 is to be associated.

The database 5 may also comprise an association 22 between the object of interest and a position 8 of the object of interest in the stored image. Consequently, the user interface may be arranged for enabling a user to select the object of interest by indicating the position 8 of the object of interest in the stored image. For example, the user may be enabled to use a pointing device to move a pointer to the position 8 when the stored image 6 is displayed.

The associating subsystem 4 may be arranged for storing in the database 5 an association 24 between the object of interest and a position 10 of the object of interest in the new image. The user interface may be arranged for enabling a user to indicate the position 10 of the object of interest in the new image, similar to the way in which the position 8 may be indicated. The associating subsystem 4 may be arranged for including an association 24 between the object of interest and the position 10, as indicated by the corresponding dashed line in FIG. 1.

The image selector 1 may be arranged for selecting the stored image 6 or the object of interest before the new image 9 is acquired.

The system may comprise a graphical subsystem 14 for displaying the stored image 6. For example, the stored image 6 may be displayed during a time interval comprising a time of acquiring the new image and a time of indicating that the new image 9 is to be associated with the object of interest. That is to say, the stored image 6 may be selected and displayed. This displayed image can be used as a reference by the user during the acquisition of the new image. The stored image may be displayed at least until a new image has been indicated to be associated with the object of interest.

The user interface 3 may be provided at least in part on the image scanner 2. For example, a button may be provided on the image scanner to indicate which newly acquired image is to be associated with the object of interest. For example, a button may be provided to enable a user to indicate that the last acquired image is the new image to be associated with the object of interest. Also, controls may be provided on the image scanner to indicate the position of the object of interest in the stored image and/or in the new image.

As an application example, the stored image 6 and the new image 9 may be breast images. In such a case, the object of interest may comprise a breast lesion.

The image scanner for acquiring the new image may comprise an ultrasound scanner.

The system may be implemented at least partly on a medical workstation having an image scanner. For example, a computer terminal with monitor, keyboard, and mouse may be provided. The image selector, user interface, and/or associating subsystem may be implemented at least partly as software installed on the medical workstation. The computer terminal may be connected to the image scanner 2, for example a hand-held ultrasound device, for example via a USB connection. The user interface 3 may be implemented at least partly on the image scanner.

Figure 2:
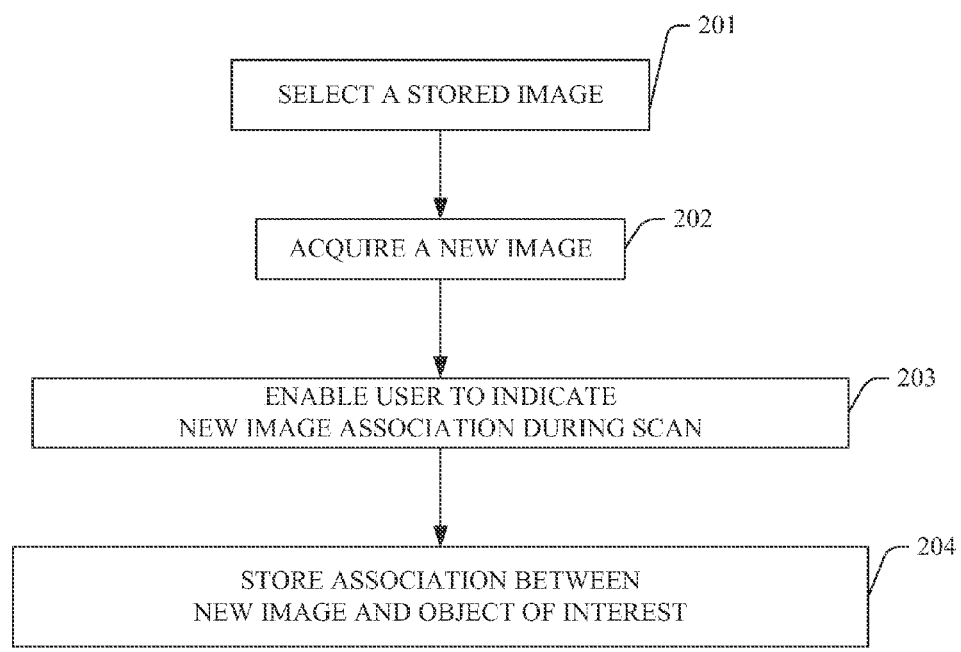
FIG. 2 is a diagram of a method of associating acquired images with objects.

FIG. 2 illustrates a flow chart of a method of associating acquired images with objects. The method may comprise selecting 201 a stored image 6 from a database comprising a plurality of stored images, the database comprising an association 21 between the stored image 6 and an object of interest. The method may further comprise acquiring 202 a new image 9 comprising a representation of at least part of the object of interest, during an imaging session. The method may further comprise enabling 203 a user, during the imaging session, to indicate that the new image 9 is to be associated with the object of interest. The method may further comprise storing 204 an association 23 between the new image and the object of interest into the database. Variations and/or additions to the method are within reach of the skilled person in view of the present disclosure. The method may be implemented at least in part by means of a computer program product comprising computer readable instructions.

In the following, the application of breast imaging by means of amongst others ultrasound imaging will be described. However, this is a non-limiting example. Other applications are possible. For example, brain imaging or cardiac imaging are also possible. Other imaging modalities are also possible, for example MR or x-ray imaging.

Using the system described above, it is possible to link the lesion currently imaged on US to its appearance on, for example, a prior MR or mammography image. This link, or association, can be established at the time of the US acquisition. This way, the number of errors may be reduced.

The graphical subsystem may be arranged for displaying prior breast images of the patient together with structured reports of individual lesions in the US room. For example, volume rendering may be used to display the patient's skin and the lesion. The database 5 may comprise a unique identifier 20 for each identified physical lesion with links to prior images and regions of interest in these images showing the lesion. The user interface 3 may be arranged for enabling the user to select one of the lesions in the database, e.g. by selecting the lesion as imaged on one or more of the available prior images. The associating subsystem 4 may be arranged for linking a newly acquired ultrasound image to a selected object of interest automatically. This automatic association may be created with help of image feature information obtained via image processing. For example, a lesion detector may be used to help to find the position of a lesion in the image as an object of interest. Alternatively, the position may be indicated by a user either manually or semi-automatically.

Figure 3:
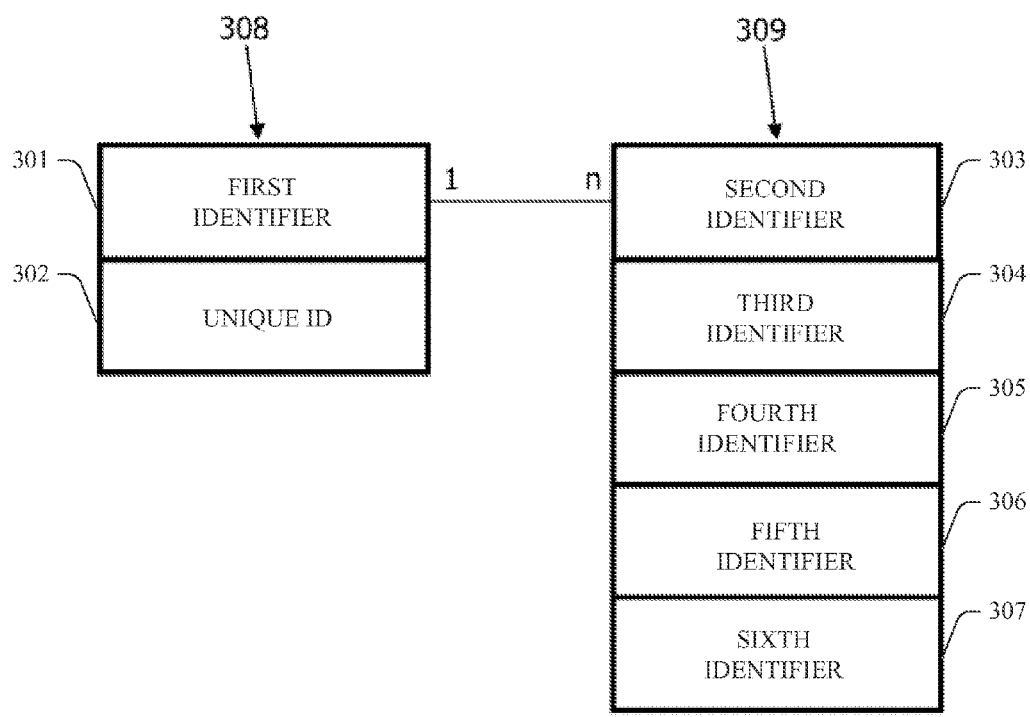
FIG. 3 illustrates a manner in which associations may be represented.

FIG. 3 illustrates an alternative manner in which the associations may be represented. The Figure shows two kinds of tables, namely an object-of-interest table 308 and an object-of-interest-image table 309. When the object of interest is a lesion, these tables may be called lesion table and lesion-image table, respectively. Such tables represent computer software objects, which may be stored in a database. By means of identifiers, such computer software objects may refer to each other to create links or associations. More kinds of tables may be provided in a database, for example additional tables linking objects of interest to patients, including derived data (segmentations and computed features) as well as radiology and pathology findings.

Illustrated in FIG. 3 are an object-of-interest table 308 and an object-of-interest-image table 309. The object-of-interest table 308 may have an identifier 301 to identify the table as an object-of-interest table. Moreover, the object-of-interest table 308 may have a unique object-of-interest ID 302. An object-of-interest table, identified by its unique object-of-interest ID 302, may represent an object of interest in the real world, for example a particular lesion in a patient. Each object of interest may be imaged by one or more imaging modalities (including Mammography, MR, US) at multiple times. For each image showing an object of interest, an object-of-interest-image table 309 may be created. An object-of-interest-image table 309 may be identified as an object-of-interest-image table by means of an identifier 303. Also, the object-of-interest-image table may have a unique object-of-interest-image table ID 304. The object-of-interest-image table 309 may be associated with an object of interest in the real world by means of a link to the corresponding object-of-interest table 308. Such a link may take the form of a copy of the object-of-interest ID 302, as illustrated at 305. The object-of-interest-image table 309 may further comprise an image identifier 306 to provide a link to an image (e.g. a stored image or a new image) showing the object of interest. Such an image identifier 306 may comprise a DICOM series UID. The location of the lesion in the image may be specified by a description of a position 307 or region of interest or volume of interest. For example, appropriate image coordinates may be provided of the center of the object of interest or of corners of a rectangle comprising the object of interest. Other shapes of a region or volume of interest are also possible, for example circular, spherical, or ellipsoidal.

The procedure of associating a new image with an object of interest in a previous, stored image, may comprise the following steps.

Based on a prior image (e.g., an MR or X-Ray image identified by its Dicom series UID) the user may select an object of interest, for example by clicking on a lesion voxel (x_lesion, y_lesion, z_lesion). Alternatively the user may be enabled to select an object of interest from the database (restricted to a specific patient) directly. The object-of-interest-image tables may then be searched for a table having the correct image identifier, and wherein the position 307 corresponds approximately to the indicated position, or wherein the indicated position is comprised in the region/volume of interest. In the case of overlapping regions/volumes of interest, this may be resolved by asking the user to select one of the regions/volumes of interest comprising the indicated position.

If no matching object-of-interest-image table is found, a new object-of-interest table 308 may be generated and a corresponding new object-of-interest-image table 309 may be generated and linked by means of the identical object-of-interest table ID 302, 305. In order to do so, the user may be asked to define the VOI containing the lesion manually or to correct or confirm an automatically proposed VOI.

The object-of-interest-image table that was retrieved or generated as described above contains the object-of-interest ID 302 to which the new image that is to be acquired will be linked.

The user may perform the US imaging procedure, looking for the same object of interest as he has indicated in the stored image.

Once an acceptable view of the object of interest has been generated, the image is stored. At the same time a new object-of-interest-image table 309 may be generated. This new object-of-interest-image table 309 may comprise the image identifier 306 (e.g. the DICOM series UID) of the new image. The user may be asked to indicate a region/volume of interest containing the object of interest or the position of the object of interest in the new image. These position data 307 may be stored in the new object-of-interest-image table 309. Alternatively, an automatic object detection algorithm may be used in order to propose a region of interest automatically. Such an automatically proposed region/volume of interest may be confirmed by the user or stored in the new object-of-interest-image table 309 automatically Optionally, an additional consistency check can be incorporated. For this purpose, the object of interest may be automatically segmented in the prior image as well as in the new image, using existing segmentation algorithms. Object features such as object size may be measured or computed based on the segmentation in both images. In the case of a significant discrepancy between the results (e.g., above 20%) the user may be alerted and can decide to revise his or her decision.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a floppy disc or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or be used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for associating acquired images with objects, comprising
    an image selector for selecting a stored image from a database comprising a plurality of stored images, the database comprising an association between the stored image and an object of interest;
    an image scanner for acquiring a new image comprising a representation of at least part of the object of interest, during an imaging session;
    a user interface for enabling a user, during the imaging session, to indicate that the new image is to be associated with the object of interest, wherein the user interface is provided at least in part on the image scanner; and
    an associating subsystem for creating an association between the new image and the object of interest in the database.

2. The system according to claim 1, wherein the user interface is arranged for enabling a user to select the object of interest from a plurality of objects of interest associated with the stored image.

3. The system according to claim 1, wherein the database comprises an association between the object of interest and a position of the object of interest in the stored image.

4. The system according to claim 3, wherein the user interface is arranged for enabling a user to select the object of interest by indicating the position of the object of interest in the stored image.

5. The system according to claim 1, wherein the associating subsystem is arranged for storing in the database an association between the object of interest and a position of the object of interest in the new image.

6. The system according to claim 5, wherein the user interface is arranged for enabling a user to indicate the position of the object of interest in the new image.

7. The system according to claim 1, wherein the image selector is arranged for selecting the stored image or the object of interest before the new image is acquired.

8. The system according to claim 1, further comprising a graphical subsystem for displaying the stored image during a time interval comprising a time of acquiring the new image and a time of indicating that the new image is to be associated with the object of interest.

9. The system according to claim 1, wherein the stored image and the new image are breast images, and the object of interest comprises a breast lesion.

10. The medical image acquisition apparatus according to claim 1, wherein the image scanner comprises an ultrasound scanner.

11. The system according to claim 1, comprising a medical workstation, and wherein the image selector, the user interface, and/or the associating subsystem are implemented at least partly in software arranged for running on the medical workstation.

12. A medical image acquisition apparatus comprising the system according to claim 1.

13. A method of associating acquired images with objects, comprising
 selecting a stored image from a database comprising a plurality of stored images, the database comprising an association between the stored image and an object of interest;
 acquiring a new image comprising a representation of at least part of the object of interest, during an imaging session;
 enabling, with a user interface on an image scanner, a user, during the imaging session, to indicate that the new image is to be associated with the object of interest; and
 creating an association between the new image and the object of interest in the database.

14. A non-transitory computer readable medium comprising instructions for causing a processor system to perform the method according to claim 13.

15. The method according to claim 13, further comprising storing in the database a second association between the object of interest and a position of the object of interest in the new image.

16. The method according to claim 15, further comprising enabling a user to indicate the position of the object of interest in the new image.

17. The method according to claim 13, further comprising selecting the stored image or the object of interest before the new image is acquired.

18. The method according to claim 13, further comprising displaying the stored image during a time interval comprising a time of acquiring the new image and a time of indicating that the new image is to be associated with the object of interest.

* * * * *